(12) United States Patent
Kaya et al.

(10) Patent No.: US 8,058,460 B2
(45) Date of Patent: Nov. 15, 2011

(54) NEAR INFRARED FLUOROPHORE FOR THE SELECTIVE LABELLING OF MEMBRANES IN CELLS

(75) Inventors: Zuhal Kaya, Heidelberg (DE); Roland Krämer, Münster (DE)

(73) Assignee: Universität Heidelberg, Heidelberg (DE)

( * ) Notice: Subject to any disclaimer, the term of this patent is extended or adjusted under 35 U.S.C. 154(b) by 25 days.

(21) Appl. No.: 12/442,876

(22) PCT Filed: Sep. 20, 2007

(86) PCT No.: PCT/EP2007/008212
§ 371 (c)(1),
(2), (4) Date: May 29, 2009

(87) PCT Pub. No.: WO2008/037394
PCT Pub. Date: Apr. 3, 2008

(65) Prior Publication Data
US 2009/0291467 A1    Nov. 26, 2009

(30) Foreign Application Priority Data

Sep. 27, 2006    (EP) ..................................... 06020334

(51) Int. Cl.
*C09B 1/16* (2006.01)

(52) U.S. Cl. ...................................................... 552/244

(58) Field of Classification Search .................... 552/244
See application file for complete search history.

(56) References Cited

U.S. PATENT DOCUMENTS

| | | | |
|---|---|---|---|
| 4,194,878 A | | 3/1980 | Birke et al. |
| 4,275,009 A | * | 6/1981 | Murdock ...................... 548/528 |

FOREIGN PATENT DOCUMENTS

| | | |
|---|---|---|
| EP | 0098522 A2 | 1/1984 |
| GB | 1342549 | 1/1974 |
| GB | 1431283 | 4/1976 |
| GB | 1544627 | 4/1979 |
| GB | 1567298 | 5/1980 |
| JP | 04122695 * | 4/1992 |
| WO | 95/09149 A1 | 4/1995 |
| WO | 99/65866 A1 | 12/1999 |
| WO | 99/65992 A1 | 12/1999 |
| WO | 01/44190 A1 | 6/2001 |
| WO | 2006/089809 A1 | 8/2006 |

OTHER PUBLICATIONS

JP 04122695 English Abstract, 1992.*

* cited by examiner

*Primary Examiner* — Barbara P Badio
(74) *Attorney, Agent, or Firm* — McDonnell Boehnen Hulbert & Berghoff LLP

(57) ABSTRACT

The present invention relates to anthraquinone derivatives which act as a fluorophore, to a process for producing said anthraquinone derivatives and their use as fluorophores for staining membranes in live or fixed cells.

3 Claims, 9 Drawing Sheets

NEAR INFRARED FLUOROPHORE FOR THE SELECTIVE LABELLING OF MEMBRANES IN CELLS

CROSS-REFERENCE TO RELATED APPLICATIONS

This application is a Section 371 U.S. national phase of international application PCT/EP2007/008212, filed Sep. 20, 2007, which claims priority from EP 06020334.6, filed Sep. 27, 2006.

FIELD OF THE INVENTION

The present invention relates to anthraquinone derivatives which act as fluorophores, to a process for producing said anthraquinone derivatives and their use as fluorophores for staining membranes in live or fixed cells.

BACKGROUND OF THE INVENTION

There are a number of amphiphilic probes available for the staining of cellular membranes which cover the UV and visible region of the spectrum. However, the commonly used membrane interactive fluorophores have fluorescent signatures which overlap those of other fluorophores used as molecular tags for examining aspects of cell biology or biological structures, including biomolecules such as proteins or nucleic acids. Due to this overlap in spectral ranges it is not possible to selectively visualize stained membrane structures without exciting at the same time other labelled cell structures or biomolecules and vice versa. However, the possibility of selective excitation of different fluorophores having non-overlapping or only marginally overlapping absorption/emission ranges is a prerequisite for the study of transport processes between different cell compartments. Moreover, the staining of membranes in plant cells using fluorophores having their absorption/emission ranges in the UV or visible region of the spectrum is problematic, since the background emission caused by naturally occurring fluorophores, such as the autofluorescence of chlorophyll, drastically reduces the signal/noise ratio which leads to a highly decreased sensitivity of the method.

Particularly, those fluorophores usually employed in the staining of membranes, such as DII, DIO or DIA have the disadvantage that their spectral ranges overlap the spectral ranges of the most common fluorescence markers such as green fluorescent protein (GFP) or YFP which have both for example emission ranges of 530 nm and below.

Selected derivatives of anthraquinone have been reported as fluorophores which display a long-wavelength emission extending into the infrared region of the spectrum. WO 99/65992 describes for example anthraquinone fluorophores which are able to stain the nucleus of a cell through intercalating into nucleic acids present in the cell nucleus. However, the anthraquinone derivatives described in WO 99/65992 are not suited to stain membranes of living or fixed cells and, moreover, the production of the respective anthraquinones is only possible in low overall yields.

Therefore, a constant need exists for a membrane interactive fluorophore having an absorption/emission range which does not or substantially not overlap with the spectral ranges of the most commonly used fluorophores which are activated in the UV or visible region.

SUMMARY OF THE INVENTION

Thus, the technical problem underlying the present invention is to overcome the above-mentioned problems by providing a novel anthraquinone fluorophore which is capable of specifically staining the membranes of live and fixed cells and has an absorption/emission range which does not or substantially not ("only marginally") overlap with the spectral ranges of the most commonly used fluorophores which are activated in the UV or visible region.

The solution to the above technical problem is achieved by providing the embodiments characterized in the claims.

DESCRIPTION OF THE DRAWINGS

FIG. 3a shows a HeLa cell which has been stained with WGA-FITC while FIG. 3b shows the same cell stained with KAYA1. FIG. 3c shows the colocalization of both images.

Figure 1A:
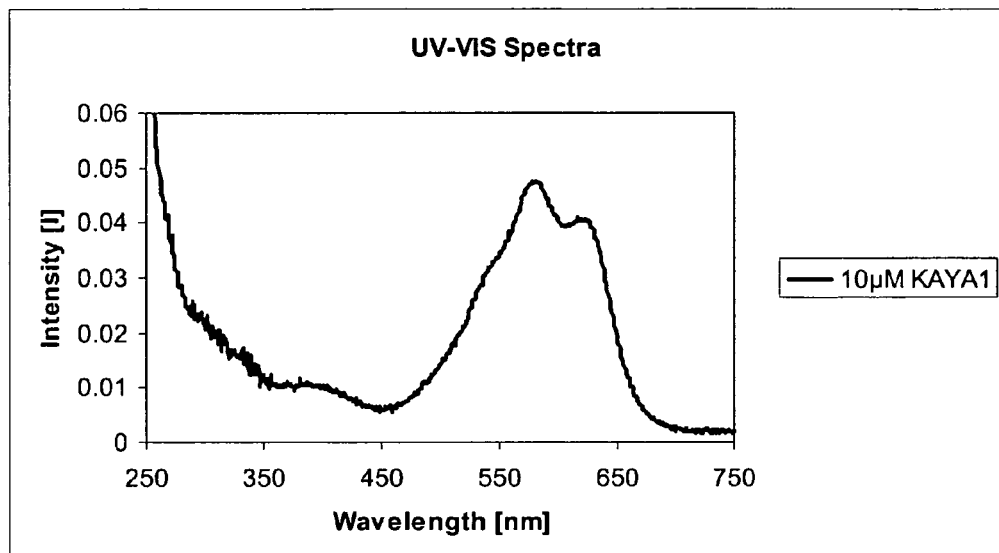
FIG. 1a shows the extinction of 10 .mu.M 1-(6-amino-hexylamino)-5-chloro-4,8-dihydroxy-anthraquinone (KAYA1) in water in the range of from 574 nm to 623 nm.
Figure 1B:
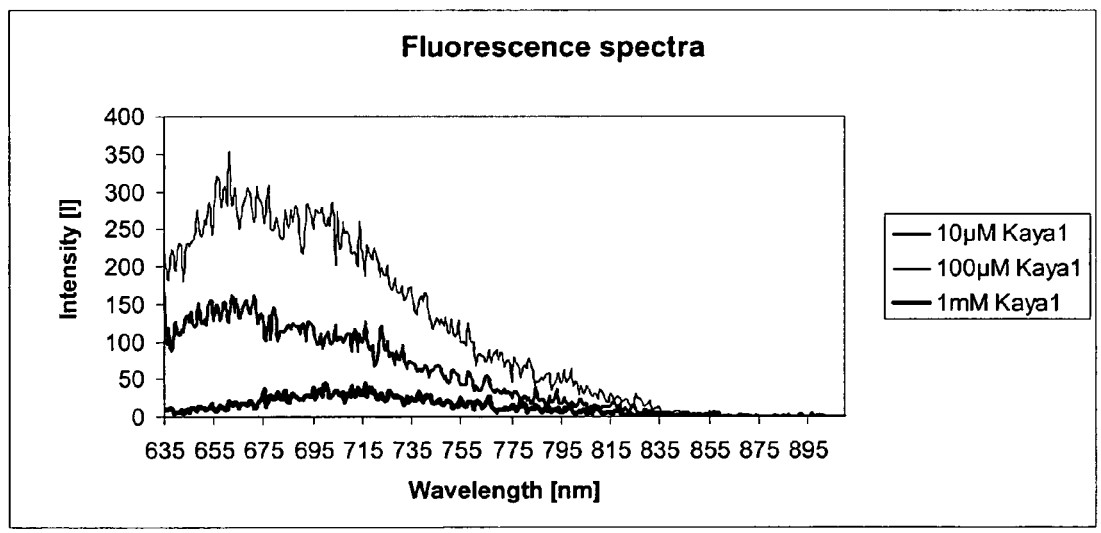
FIG. 1b shows the emission of KAYA1 in concentrations of 10 .mu.M, 100 .mu.M and 1 mM on excitation at 623 nm in a MOPS-buffered aqueous solution at pH 7.

In particular, there is provided an anthraquinone fluorophore of the following general Formula I:

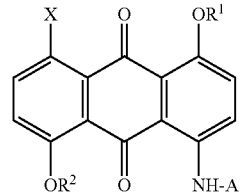

Formula I wherein X is hydrogen, halogen, $OR^5$ or $NR^6R^7$, A is a $C_1$-$C_{24}$ alkyl group optionally substituted with one or more hydroxy, carboxy or thiol group(s), or Y—$NR^3R^4$; $R^1$ to $R^7$ may be the same or different and each of $R^1$ to $R^7$ is independently selected from hydrogen, $C_1$-$C_{12}$ alkyl, $C_1$-$C_{12}$ alkenyl and aryl; and Y is an aromatic or aliphatic spacer having 5 or more carbon atoms.

The term "fluorophore" used herein means a functional group and/or a molecule containing said functional group which will absorb energy of a specific wavelength and re-emit energy at a different wavelength.

The term "alkyl" used according to the present invention is not specifically restricted. It includes any group which is a straight chain or a branched chain group, preferably containing 1 to 12 carbon atoms, more preferably 1 to 8 carbon atoms. Examples of such alkyl groups are methyl, ethyl, propyl, 2-propyl, n-butyl, t-butyl, pentyl, hexyl, cyclohexyl, octyl, decyl, undecyl or dodecyl.

Similarly, the term "alkenyl" used herein is not specifically restricted. It includes any group which is a straight chain or a branched chain group, preferably containing 1 to 8 carbon atoms, and has at least one double bond. Examples of alkenyl groups are propenyl, 1-butenyl, 2-butenyl, 1-pentenyl, 2-pentenyl, 3-pentenyl, 1,3-pentadienyl, 1,3,5-hexantrienyl, 3-methyl-3-hexenyl, 2-decenyl or 10-dodecenyl.

The residue A may be for example an alkyl group having 1 to 24 carbon atoms, preferably 12 to 20 carbon atoms and more preferably 15 to 18 carbon atoms. Moreover, said alkyl group may be substituted by one or more hydroxy, carboxy or thiol group(s). According to a preferred embodiment of the present invention, A may be a straight chain alkyl group having 12 to 18 carbon atoms and being unsubstituted or being substituted with a hydroxy, carboxy or thiol group preferably on its terminal end. Examples of A according to the present invention include —$(CH_2)_{15}$—$CH_2OH$, —$(CH_2)_{17}$—$CH_3$ and —$(CH_2)_{19}$—$CH_2SH$.

Moreover, the term "aromatic spacer" means according to the present invention any aromatic group, i.e. any group having delocalized π-electrons, and is no further restricted in any way. Examples of such aromatic spacers are phenyl, biphenyl, naphthalene, cyclopentadienyl anion, cycloheptatrienyl cation, and derivatives thereof.

The term "aliphatic spacer" used herein includes any non-aromatic organic group which may contain one or more double or triple bonds. Said aliphatic spacer may be a straight chain, branched or cyclic compound, or any derivative thereof. Examples of such aliphatic spacers are alkyl groups such as pentylene, hexylene, heptylene and octylene groups, or alkenylene groups such as 1-butenylen, 2-butenylen, 3-pentenylen and 2-hexenylene. Said term "aliphatic spacer" also includes alkynylene groups such as 3-pentynylene or 2-hexynylene.

One embodiment of the present invention relates to the anthraquinone fluorophore as defined above, wherein Y is an aromatic or aliphatic spacer having 5 to 12 carbon atoms. In a preferred embodiment of the present invention Y is an aliphatic (e.g. straight chain) alkylene group having 5 to 12 carbon atoms. Preferably the aliphatic (e.g. straight chain) alkylene group comprises 5 to 10 carbon atoms, more preferably 6 to 8 carbon atoms, and most preferably 6 carbon atoms.

In a specific embodiment according to the present invention in the anthraquinone fluorophore as defined above, X represents chlorine, R represents hydrogen and Y represents an n-hexylene group.

The anthraquinone fluorophore of the present invention does not only include the above-defined compound as such, but may also be present in form of a salt or in its protonated or deprotonated form, as long as this has no undue negative impact on the desired chemical, biological and physical, particularly spectroscopic, properties of said anthraquinone fluorophore. According to a specific embodiment of the present invention, the anthraquinone fluorophore as defined above is present in form of its ammonium salt.

The fluorophore according to the present invention may further be part of a bioconjugate. The fluorophore may e.g. be attached to a biologically active molecule such as nucleic acids like DNA, RNA, PNA, proteins (e.g. streptavidin/avidin), peptides or biotin. These bioconjugates may for example be used to specifically target certain biological structures of living or fixed cells.

According to another embodiment of the present invention, the anthraquinone fluorophore as defined above absorbs and/or emits light of a wavelength in the range of from 500 to 950 nm, preferably from 525 to 900 nm, and more preferably from 550 to 850 nm. According to a specific embodiment of the present invention, the above-defined anthraquinone fluorophore absorbs and/or emits light of a wavelength in the range of from 575 to 830 nm.

In one specific example of the present invention, the emission of the fluorophore is in the range of from 630 to 835 nm.

Another aspect of the present invention relates to a process for producing an anthraquinone fluorophore of the following general Formula I:

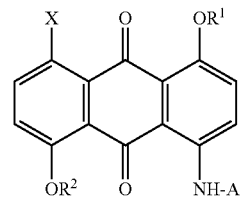

Formula I wherein X is hydrogen, halogen, $OR^5$, $NR^6R^7$, or NH—Y—$NR^3R^4$, wherein A is a $C_1$-$C_{24}$ alkyl group optionally substituted with one or more hydroxy, carboxy or thiol group(s), or Y—$NR^3R^4$; $R^1$ to $R^7$ may be the same or different and each of $R^1$ to $R^7$ is independently selected from hydrogen, $C_1$-$C_{12}$ alkyl, $C_1$-$C_{12}$ alkenyl and aryl; and Y is an aromatic or aliphatic spacer having 5 or more carbon atoms, comprising the steps of:
(a) halogenating a starting compound represented by the Formula II:

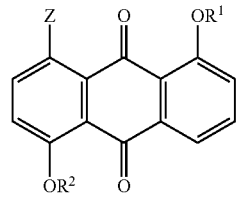

Formula II using a halogenating agent, wherein Z is independently selected from hydrogen, halogen, $OR^5$ or $NR^6R^7$ and each of $R^1$ to $R^7$ is as defined above;
(b) reacting said halogenated compound with an amino compound of the general formula $H_2N$-A, wherein A is a $C_1$-$C_{24}$ alkyl group optionally substituted with one or more hydroxy, carboxy or thiol group(s), or Y—$NR^3R^4$, Y—NQ, Y—NHQ, Y—$NH_2Q$ or Y—$NH_3Q$; Y is an aromatic or aliphatic spacer having 5 or more carbon atoms; $R^3$ and $R^4$ are independently selected from hydrogen, $C_1$-$C_{12}$ alkyl, $C_1$-$C_{12}$ alkenyl or aryl, with the proviso that $R^3$ and $R^4$ are not both hydrogen; and Q is a protecting group; and (c) if a protecting group is present, deprotecting the protected amino group using a deprotecting agent.

According to the present invention the groups X, Y and each R are the same as defined above. In a preferred embodiment of the process of the present invention, Z, $R^1$ and $R^2$ are hydrogen, and in a more preferred embodiment X, Z, $R^1$ and $R^2$ are hydrogen and Y is n-hexylene.

The term "halogenating agent" used herein relates to any compound which is capable of introducing one or more halogen atoms into an organic compound. According to one embodiment of the present invention the halogenating agent is selected from dihalogen, sulfurylhalogenide, thionylhalogenide or N-halogen succinimid, hydrogenhalogenide, phosphorylhalogenide, halophosphine, triphosgen (BTC), boronhalogenide and trihalogene acetate.

The expression "protecting group" is not especially restricted and includes any chemical group which can be reversibly bound to a primary, secondary or tertiary amino group and can be removed under special conditions in a deprotecting step. The compounds of the general formula $H_2N$—Y—$NR^3R^4$, $H_2N$—Y—NQ, $H_2N$—Y—NHQ, $H_2N$—Y—$NH_2Q$ or $H_2N$—Y—$NH_3Q$ are not limited as such and further include those forms thereof having negative or positive charges. It is preferable to choose the protecting group according to the desired reaction step to be carried out. Examples of such protecting groups are groups used in peptide or protein synthesis.

According to one embodiment of the present invention, in the process as defined above the protecting group Q of the diamino compound is selected from Boc, Fmoc, Z-group, phthalimide, Cbz/Z and Alloc.

In a specific embodiment of the process as defined above, the protected diamino compound is Boc-1,6-diaminohexane.

A further aspect of the present invention relates to a use of an anthraquinone fluorophore of the general Formula I:

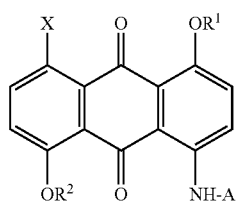

Formula I wherein X is hydrogen, halogen, $OR^5$, $NR^6R^7$ or NH—Y—$NR^3R^4$, A is a $C_1$-$C_{24}$ alkyl group optionally substituted with one or more hydroxy, carboxy or thiol group(s), or Y—$NR^3R^4$; $R^1$ to $R^7$ may be the same or different and each of $R^1$ to $R^7$ is independently selected from hydrogen, $C_1$-$C_{12}$ alkyl, $C_1$-$C_{12}$ alkenyl and aryl; and Y is an aromatic or aliphatic spacer having 5 or more carbon atoms, for visualizing, analyzing and/or imaging cell membranes in live or fixed cells.

In one example of the present invention, the above-defined fluorophore is used for visualizing, analyzing and/or imaging cell membranes in live or fixed cells outside the living animal or human body.

The expression "visualizing cell membranes" according to the present invention includes all those methods which can be used for visualization of biological processes, biomolecules and/or cellular structures of living or fixed animal or plant cells, for example human cells. Examples of such methods are flow cytometry, fluorescence microscopy, confocal laser scanning microscopy (CLSM) and light optical microscopy.

The anthraquinone fluorophore of the present invention is particularly specific for cell membranes. However, said cell membranes are not limited to a specific type of membrane but include, for example, nuclear membranes and cell membranes of a variety of organelles, such as golgi apparatus or endoplasmatic reticulum.

Moreover, the fluorophore according to the present invention may be used for staining other biological or chemical structures such as viruses or vesicles. The type of biological structure for which the fluorophore of the present invention is usable is therefore not limited as long as it exhibits the desired chemical and physical properties necessary for the use defined above.

According to one embodiment of the present invention, in the use as defined above the cells are treated with a composition comprising the anthraquinone fluorophore, said fluorophore is excited inside the cell using a suitable light source and the fluorescence of said fluorophore is detected.

The expression "suitable light source" as used herein is not especially restricted and includes any light source known in the art which is usable to excite a fluorophore. According to a preferred embodiment of the present invention, the light source emits a small specific range of the spectrum, such as a laser.

According to one embodiment of the present invention, in the use as defined above the light source emits light at a wavelength in the range of from 450 to 1200 nm, preferably in the range of from 475 to 900 nm and more preferably in the range of from 500 to 800 nm.

Further, the fluorescence of the anthraquinone fluorophore in the use as defined above occurs at a wavelength in the range of from 500 to 950 nm, preferably in the range of from 525 to 900 nm, and more preferably in the range of from 550 to 850 nm. According to a specific embodiment of the present invention, in the use as defined above the fluorescence of said anthraquinone fluorophore occurs at a wavelength in the range of from 575 to 830 nm.

In one specific example of the present invention, in the use as defined above, the emission of the fluorophore is in the range of from 630 to 835 nm.

Another embodiment of the present invention relates to the afore-defined use, wherein the anthraquinone fluorophore is used in combination with at least one other fluorophore, wherein the at least one other fluorophore absorbs and/or emits light at a different wavelength.

The term "other fluorophore" used herein includes any fluorophore or molecule containing said fluorophore which can be used in combination with the anthraquinone fluorophore as defined above. Examples of said other fluorophore are commercially available and known in the state of the art and are such fluorophores which absorb and/or emit light in the UV or visible spectrum.

According to a preferred embodiment of the present invention, the at least one other fluorophore is selected from fluorescein derivatives such as FITC, GFP, YFP, rhodamine derivatives, Cy-dyes such as Cy3 or Cy5, CFP, ceru, mRFP, DAPI, BODIPY, or any combination thereof.

Another aspect of the present invention relates to a kit, which comprises the above-defined anthraquinone fluorophore, and optionally one or more auxiliary agents selected from solvents, diluents, buffers and salts, and one or more other fluorophores. The above-defined anthraquinone fluorophore may for example be present in the kit in a dissolved form, as a dispersion or as a solid.

Further, the kit of the present invention may for example contain the anthraquinone fluorophore according to the present invention and further components usable in staining specific portions of a live or fixed cell, such as biological structures of interest and/or biomolecules such as proteins or nucleic acids. The kit according to the present invention preferably contains one or more other fluorophores and can be used for treating cells in multicolor labelling experiments.

According to the present invention, a multicolor labelling experiment entails the deliberate introduction of two or more probes to simultaneously monitor different biochemical functions, biomolecules, and/or biological structures. For example, by using the membrane specific anthraquinone fluorophore of the present invention, in combination with a protein fluorescence marker such as GFP, it can be monitored into which organelles and past which membranes the labelled protein is transported inside the cell. As a further example, the fluorophore defined in the present invention can be used in fluorimetric cell migration assays.

The anthraquinone fluorophores of the present invention are advantageously effective in the labelling of membranes of live or fixed cells. It is especially surprising that the anthraquinone fluorophores of the present invention show an absorption range which extends up to the near infrared spectrum and thus does not or only marginally, unlike the majority of the available membrane specific fluorophores, overlap with the typical UV- and/or visible absorption/emission ranges used in most biological fluorescence probes such as FITC, GFP, YFP, rhodamine or BODIPY. Therefore, the fluorophores of the present application are advantageously suitable to be applied in multicolor labelling experiments, wherein the cells are treated with a variety of different fluorescence probes and the successive excitation using the specific wavelengths of each applied probe delivers a multicolor image of the desired portions of said cell.

The present invention will be further illustrated in the following examples, without any limitation thereto.

EXAMPLES

Example 1

Synthesis and Characterization of Anthraquinone Fluorophore 1-(6-amino-hexylamino)-5-chloro-4,8-dihydroxy-anthraquinone (KAYA1)

1-(6-amino-hexylamino)-5-chloro-4,8-dihydroxy-anthraquinone (KAYA1) is prepared from commercially available 1,5-Dihydroxy-anthraquinone in a three-step reaction. The starting compound is converted into 1,5-dichloro-4,8-dihydroxy-anthraquinone by treatment with sulfurylchloride in 49.5% yield after recrystallization according to a procedure described in Allen, C. F. H., Frame, G. F., Wilson, C. V., The Structures Of The So Called Toluidine Blue, *Journal of Organic Chemistry*, 1941, (6), 732-749. Reaction of 1,5-Dichloro-4,8-dihydroxy-anthraquinone with the monoprotected diamine N-Boc-1,6-diaminohexane in anisole (130° C.) yields after deprotection and chromatographic purification the title compound in 67.7% yield.

Synthesis of KAYA1:

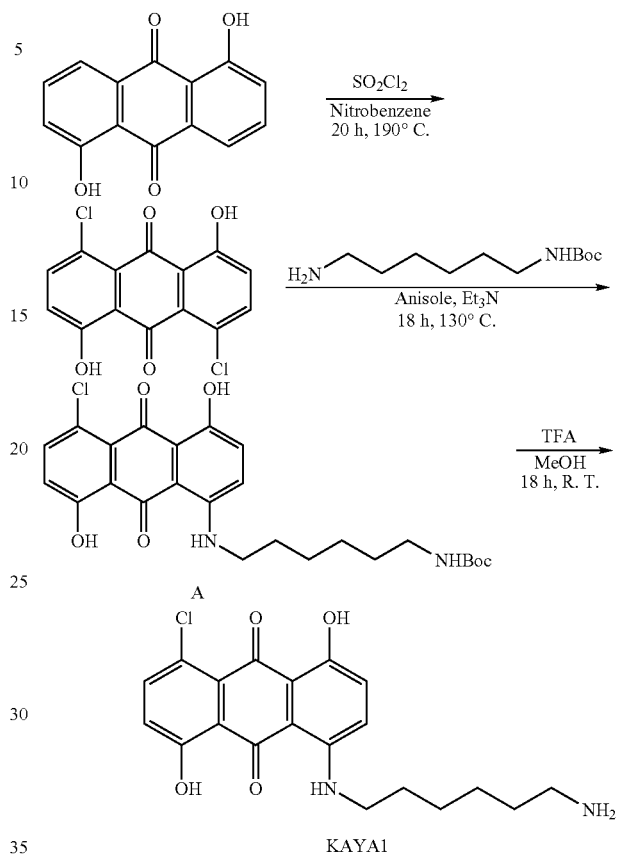

Procedure:

1,5-Dihydroxy-anthraquinone (10 g, 42 mmol) is dissolved in nitrobenzene. After addition of 10 ml $SO_2Cl_2$ (0.123 mol) the mixture is refluxed for two hours. An additional amount of $SO_2Cl_2$ (10 ml) was added dropwise and the reaction mixture is refluxed for further 20 hours. The excess $SO_2Cl_2$ is removed by heating to 210° C. Then the crude 1,5-dichloro-4,8-dihydroxy-anthraquinone is filtered and washed first with methanol and then with ether. The red compound is recrystallized from anisole.

N-Boc-1,6-diaminohexane (1 g, 4.62 mmol) and 1,5-Dichloro-4,8-dihydroxy-anthraquinone (0.71 g, 2.33 mmol) are dissolved in anisole. After addition of 700 μl triethylamine (5 mmol) the reaction mixture is refluxed at 130° C. for 18 hours. The deep blue anthraquinone derivative (A) is purified by column chromatography ($SiO_2$, 99:1 $CH_2Cl_2$/MeOH) after evaporation of the reaction solution.

The Boc protecting group of compound A is cleaved with trifluoro acetic acid (6.7 ml, 87 mmol) in methanol (3 ml, 74 mmol) for 18 hours at room temperature. After evaporation and recrystallization in anisole KAYA1 was characterized by electrospray mass spectrometry: ($M_{found}$ 389.1245 m/e, 391.1611 m/e, $M_{calc}$ 388.12 m/e, 390.12 m/e); 1H NMR spectroscopy ($CD_3OD$): S=1.39 ppm (m, 4H), 1.59 ppm (m, 2H), 1.64 ppm (m, 2H), 2.80 ppm (t, 2H), 3.24 ppm (t, 2H), 7.03 ppm (d, 1H), 7.08 ppm (d, 1H), 7.42 ppm (d, 1H), 7.65 ppm (d, 1H), 7.92 ppm (s, 1H); UV-Vis spectrophotometry ($Abs_{max}$: 574 nm and 623 nm) and fluorimetry ($Em_{max}$: 660 nm). KAYA1 is soluble in methanol and moderately soluble in water.

Example 2

Staining Protocols

In Vivo Labelling:

A protocol for the labelling of live cells was optimized for cultured HeLa cells (epithelial, cervical carcinoma), for LnCAP (Prostatacancer, fibroblasts) and VH7 (foreskin fibroblasts) that are adhering to coverslips. Cells are cultured on coverslips in DEMEM (VH7, HeLa) RPMI (LnCAP) with 10% foetal calf serum, 1 mM glutamine and antibiotics and incubated at 37° C. in an atmosphere of 5% $CO_2$. A 5 µM solution of KAYA1 is prepared in a HEPES-Glucose buffer medium containing 115 mM NaCl, 1.2 mM $CaCl_2$, 1.2 mM $MgCl_2$, 1.2 mM $K_2HPO_4$, 20 mM HEPES, 10 mM Glucose, pH 7.4. After removing the cell medium the cells are incubated with the labeling solution for 1 minute at 37° C. The labeling solution is removed, the cells washed in 1×PBS and incubated with the cell medium, prior to analysis.

In Vitro Labelling:

Staining the cell membranes of fixed cells is also compatible with KAYA1. For staining, the cells are cultured at the same conditions as described for in vivo labelling. The cells are fixed with HEPEM buffer containing 3.7% formaldehyde, 65 mM PIPES, 30 mM HEPES, 10 mM EGTA, 2 mM $MgCl_2$, pH 6.9 for 15 min. Then the cells are washed twice with 1×PBS for 7.5 min. Finally the cell membranes are stained with KAYA1 (5 µM in 1×PBS) for 5 minutes at 37° C., washed with 1×PBS and covered with Vectashield.

Example 4

Confocal Laser Scanning Microscopy (CLSM)

The System used was a Leica DM IRBE (TSC/SP2) microscope operating with a helium/neon laser. Detection of all probes was visualized with the laser emission line 633 nm, the detection window was realized between 650 nm-800 nm.

CLSM allows the blur from out of focus regions of the fluorescent specimen to be blocked, resulting in crisp, sharp images from well defined planes in the axial direction. Therefore the images presented here show well defined optical sections in z-axis of the microscope.

Example 5

Colocalization Experiments with Wheat-Germ Agglutinin (WGA)

Figure 2A:
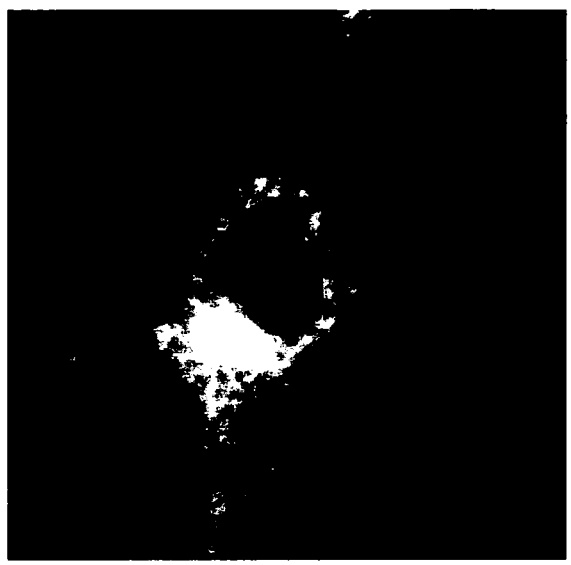
FIGS. 2a to 2c show images of membrane labelled live HeLa cells. The FIGS. 2a to 2c show representative images of live cells after incubation with a KAYA1 labelling solution. The dye visualizes the cytoplasmatic membrane, the nuclear membrane and the membrane of certain organelles such as endoplasmatic reticulum and golgi apparatus.
Figure 2B:
Figure 2C:
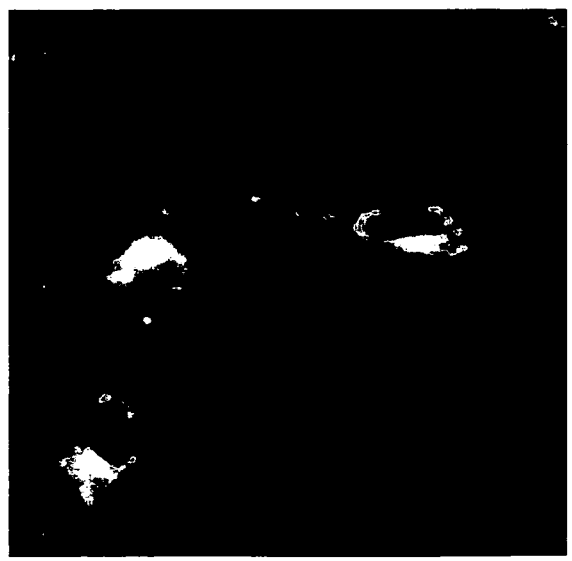
Figure 3A:
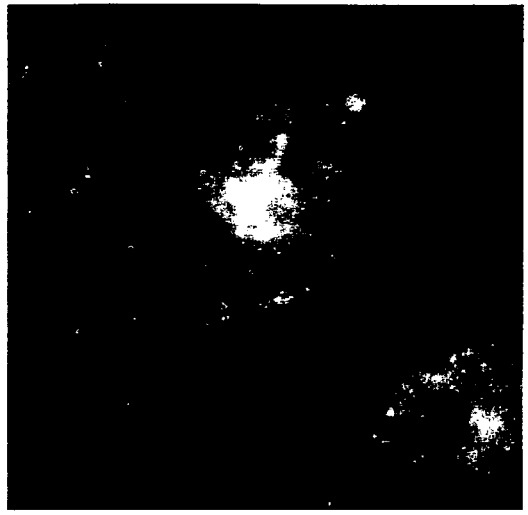
FIGS. 3a to 3c show stained images of a HeLa cell.
Figure 3B:
Figure 3C:
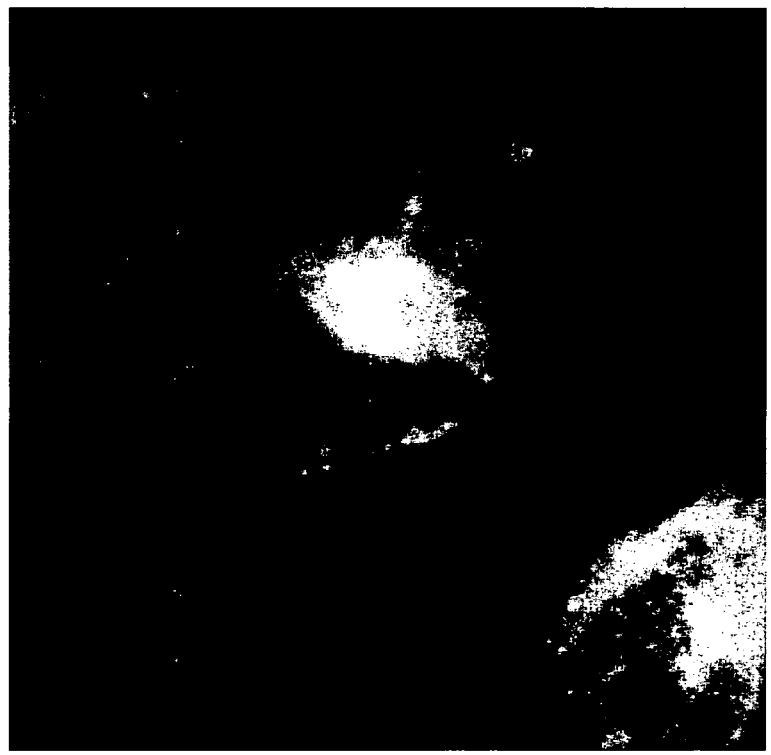
Figure 4A:
FIGS. 4a to 4c show images of KAYA1-stained HeLa cells after an incubation period of 15 hours for cell division studies.
Figure 4B:
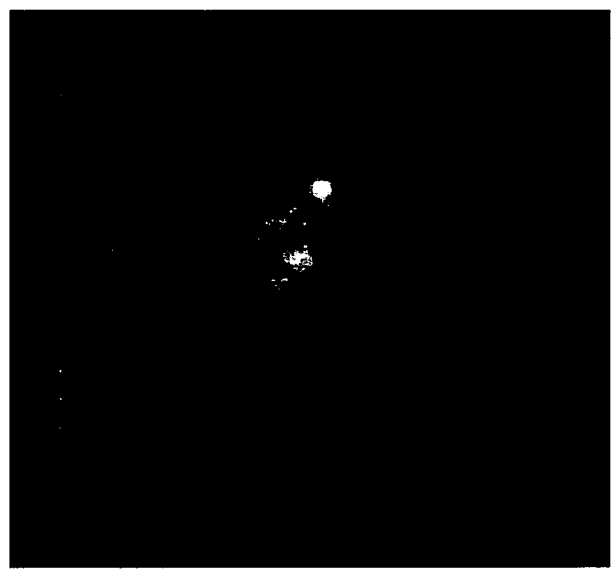
Figure 4C:
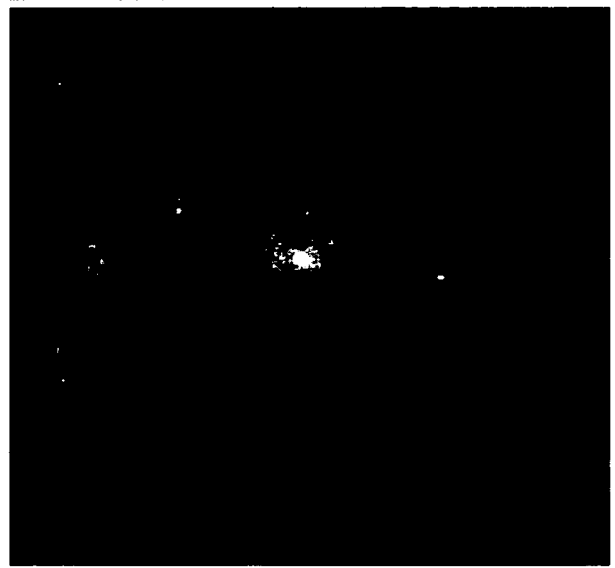
Figure 5A:
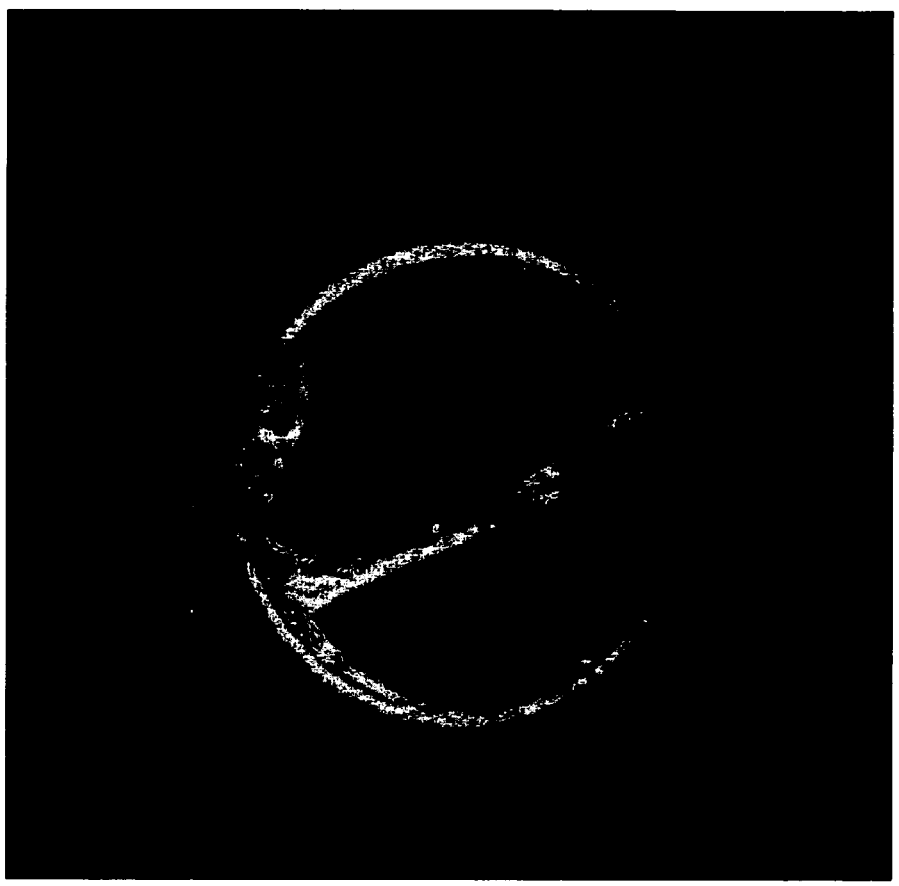
FIGS. 5a and 5b show confocal laser scanning of a plant cell (tobacco, wildtype MDB cells) which have been in vivo-stained using a concentration 10 .mu.M Kaya1 and a diffusion time of 10 to 15 min. The excitation was performed at 633 nm while the detection was carried out from 657 nm (Zeiss).
Figure 5B:
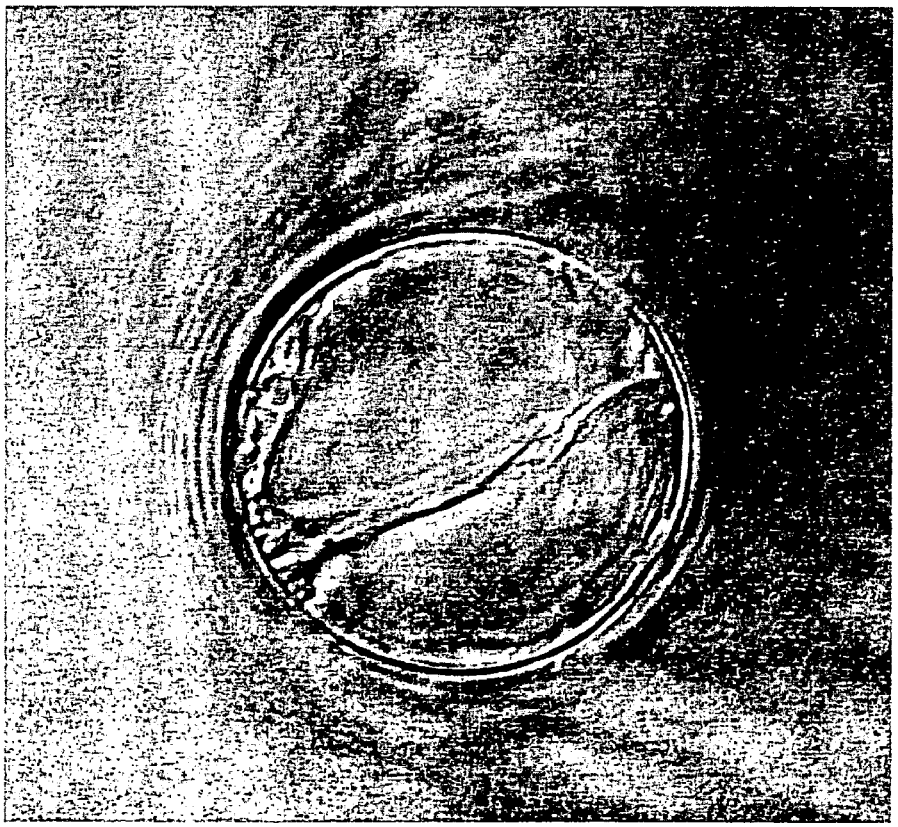
Figure 6A:
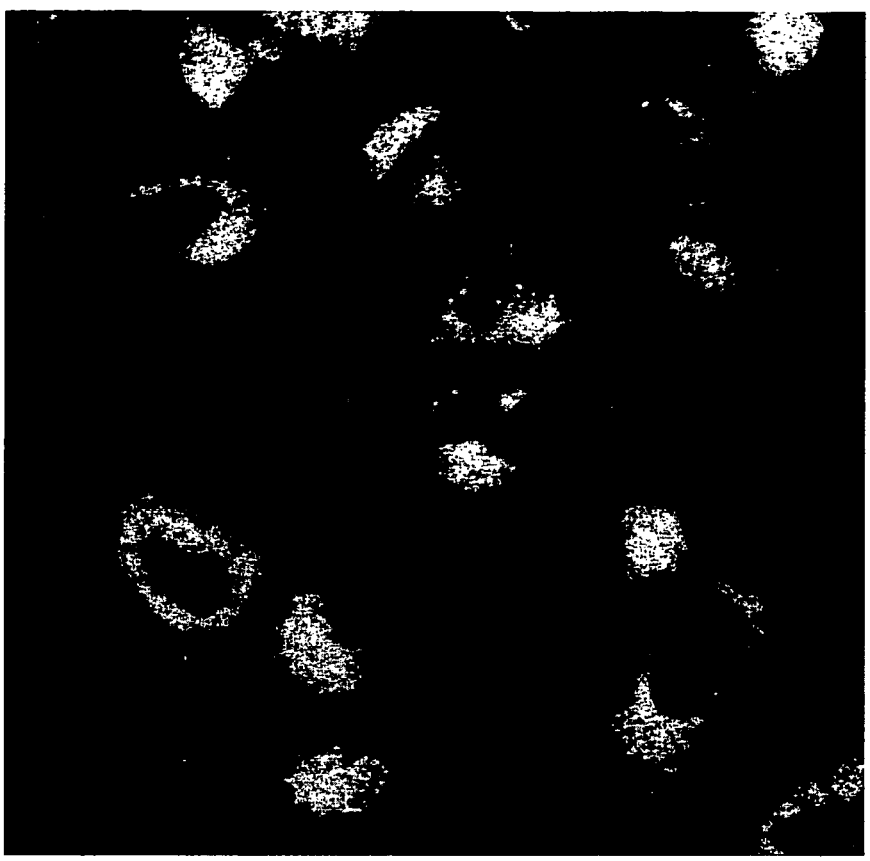
FIGS. 6a and 6b show confocal laser scanning microscopy images of HeLa cells which have been incubated for 1 min using 5 to 7.5 .mu.M 1,5-Bis-(6-amino-hexylamino)-4,8-di-hydroxy-anthraquinone (KAYA2).
Figure 6B:
Figure 7A:
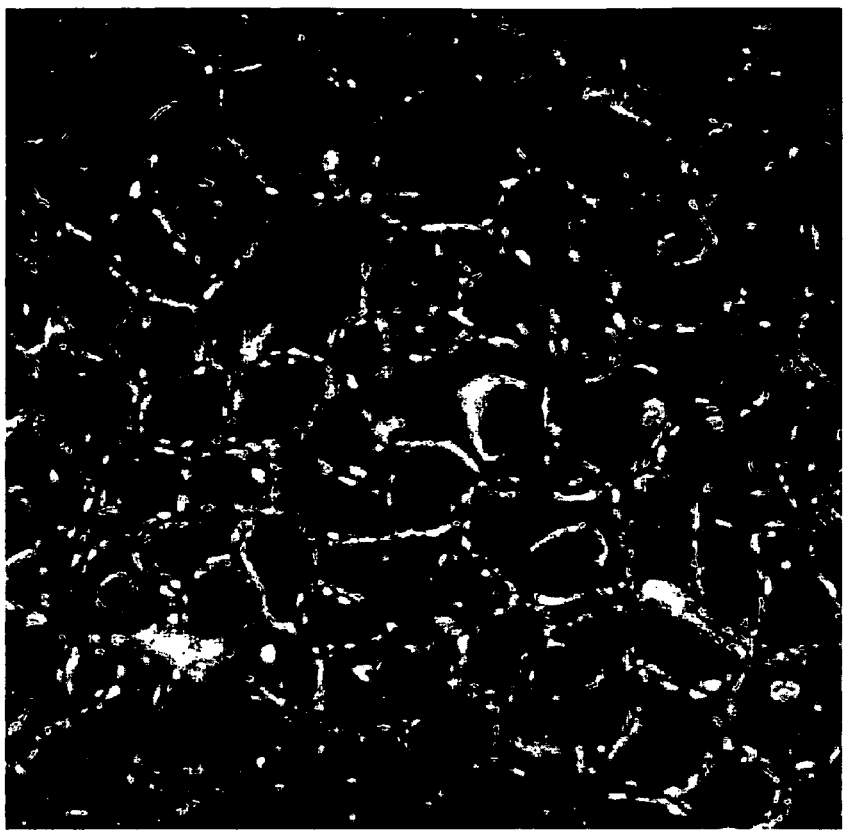
FIGS. 7a and 7b show images of epithelial cells (PFA-fixed, tissue sections) of the human small intestine. Cells have been stained using 10 .mu.M Kaya1 (FIG. 7a) and Kaya 2 (FIG. 7b).
Figure 7B:
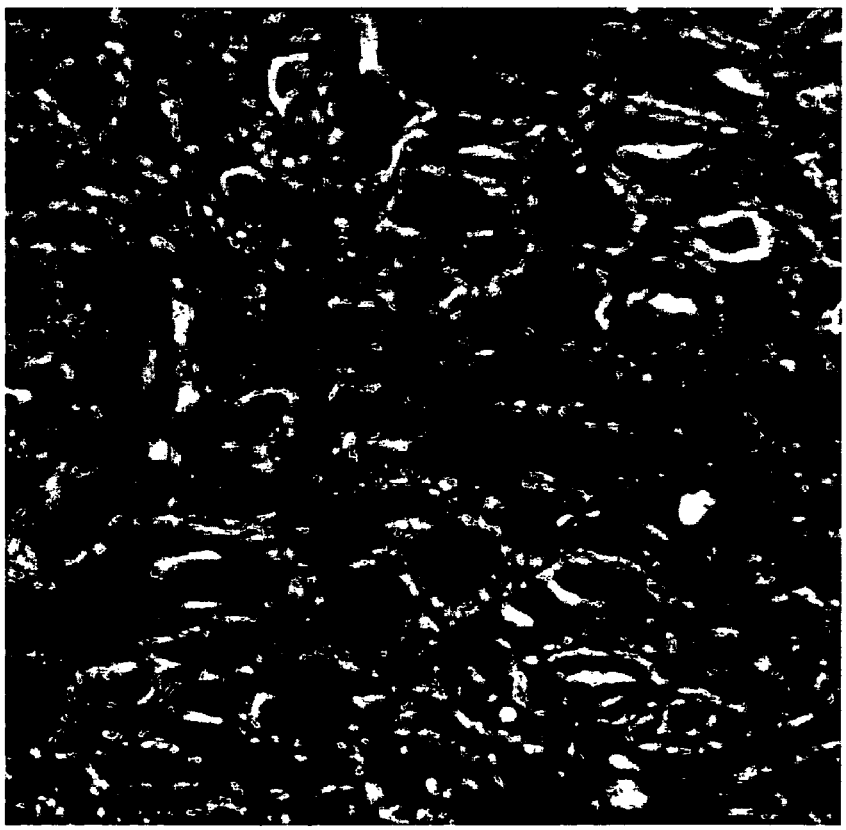
Figure 8A:
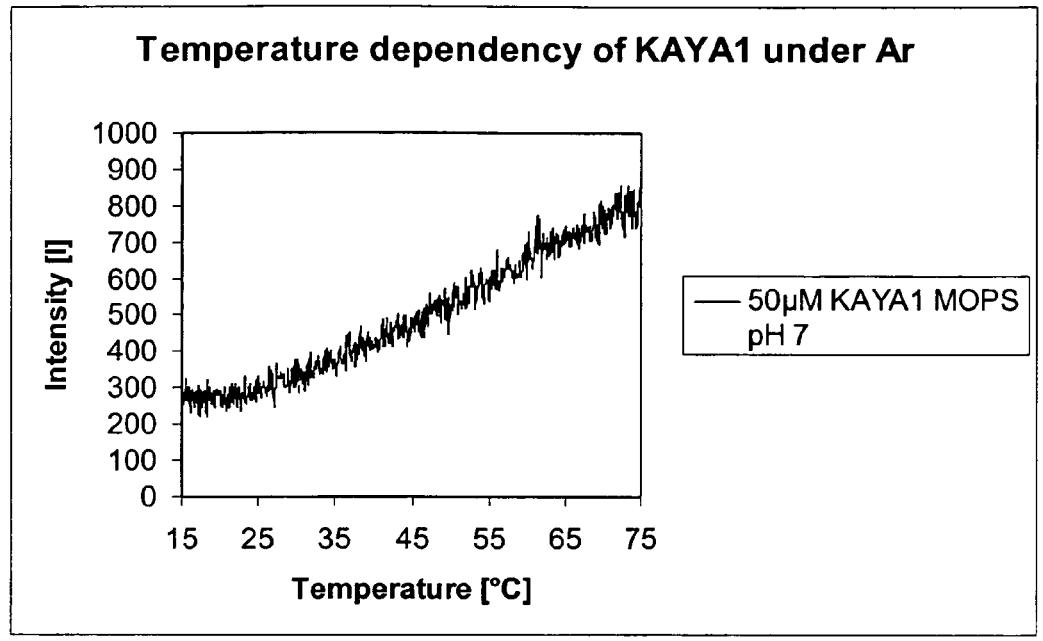
FIGS. 8a and 8b show diagrams of the temperature dependency of 50 .mu.M KAYA1 and KAYA2 solutions in MOPS buffer at pH 7.
Figure 8B:
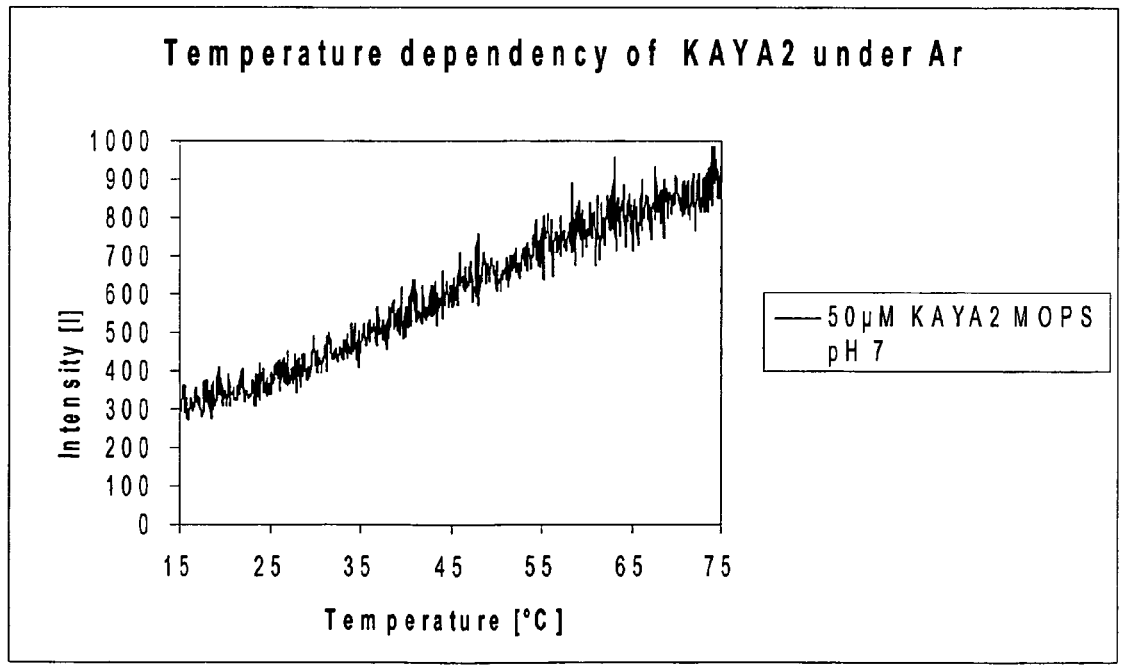
Figure 9A:
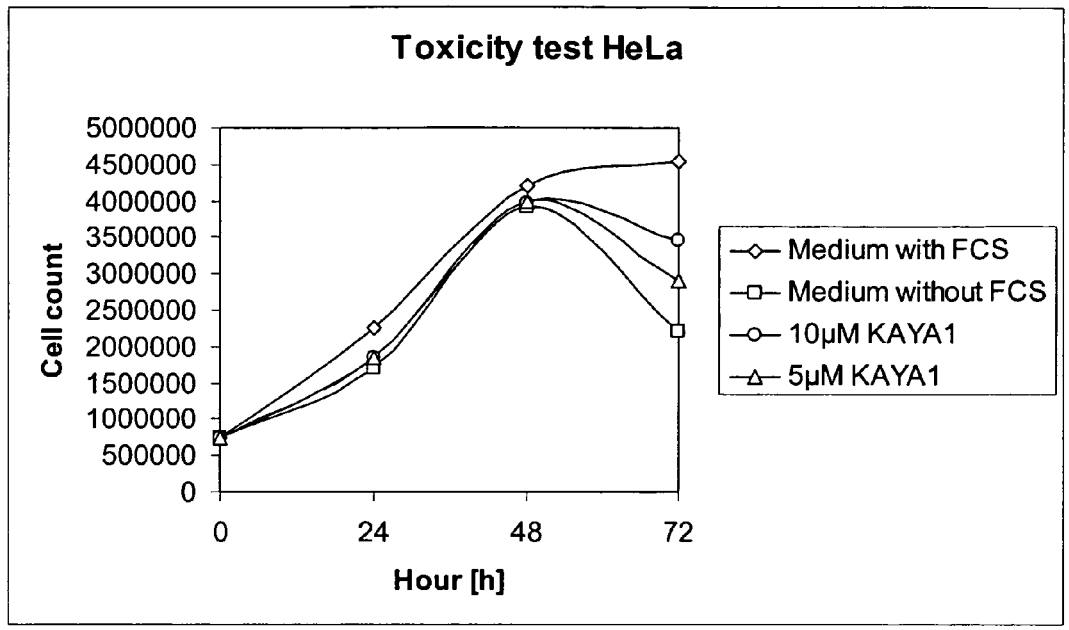
FIG. 9a shows a diagram of KAYA1 toxicity tests using HeLa cells. Division of HeLa cells takes place every 14 hours.
Figure 9B:
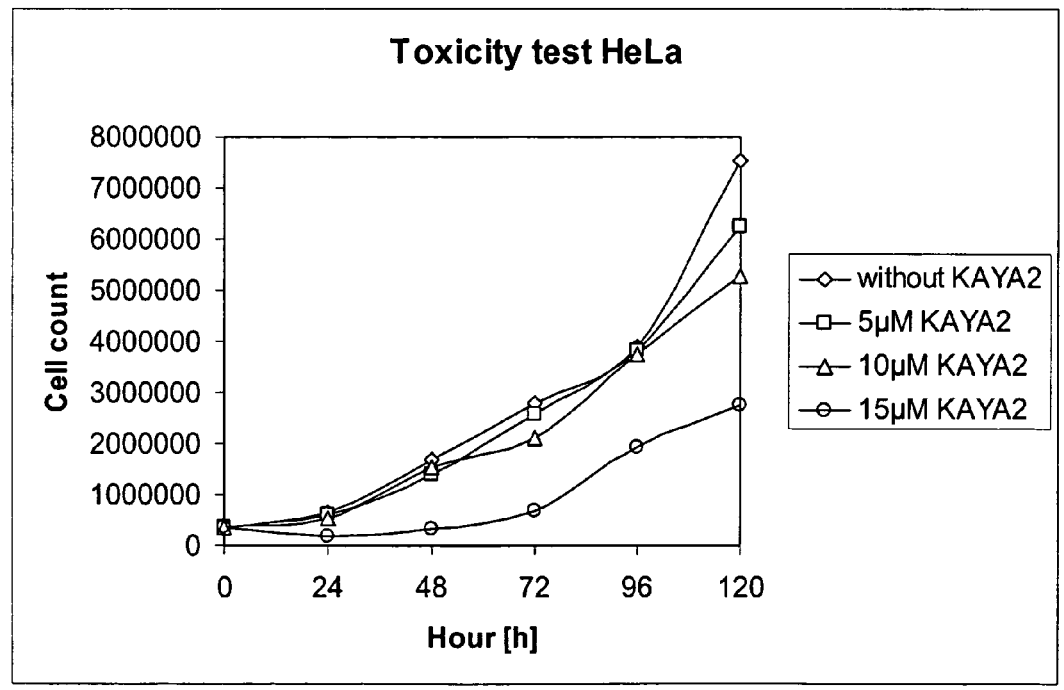
FIG. 9b shows a diagram of KAYA2 toxicity tests using HeLa cells.

Wheat-germ agglutinin (WGA) is a glycoprotein (lectin) that recognizes and binds to specific glycoconjugates such as N-acetylneuraminic acid, N-acetyl glucosamine, membrane glycoprotein, chitin, cartilage, glucosamineglycans, glycolipids, and glycoproteins with sialic acid residues (cf. Monsigny M., Roche A-C., Sene C., raget-Dana R., Delmotte F., Sugar-Lectin Interactions: How does Wheat-germ Agglutinin bind Sialoglycoconjugates?, *Eur. J. Biochem.*, 1980, (104), 147-153; Wright C S., Crystal structure of a wheat germ agglutinin/glycophorin-sialoglycopeptide receptor complex. Structural Basis for cooperative lectin-cell binding, *J. Biol. Chem.*, 1992, 267(20), 14345-52). WGA is commonly used to stain the golgi apparatus, nuclear envelop and plasma membrane of fixed cells. In vivo stains with KAYA1 (cf. for example FIGS. 2a to 2c) illustrate a high similarity with the specific binding regions of WGA in fixed cells. For fixed cells a protocol was optimized to illustrate the similarity of the binding regions of WGA and KAYA1 shown in FIG. 3a to 3c.

Colocalization Protocol of WGA and KAYA 1:

For the colocalization experiments the cells are stained with KAYA1 at the same conditions as described for in vivo labelling. Then the cells are fixed with HEPEM buffer and the membranes of the cells are permeabilized 30 min at 4° C. with 50 ml 1×PBS containing 50 mg Saponin. After washing the cells with 1×PBS for 5 min at room temperature the cells are incubated 15 min with 50 µg/ml WGA at 37° C. Finally the cells are washed with 1×PBS and covered with Vectashield, prior to analysis.

What is claimed:

1. An anthraquinone fluorophore of the following general Formula I:

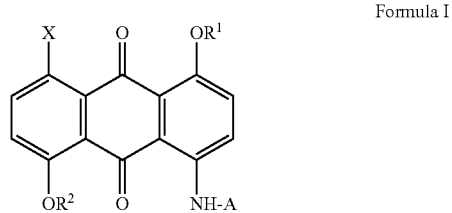

Formula I wherein X is Cl, A is $(CH_2)_6NH_2$; and $R^1=R^2=H$ or ammonium salt thereof.

2. The anthraquinone fluorophore according to claim 1, wherein the anthraquinone fluorophore absorbs and/or emits light of a wavelength in the range of from 575 to 830 nm.

3. A kit which comprises the anthraquinone fluorophore according to claim 1, and optionally one or more auxiliary agents and optionally one or more other fluorophores.

* * * * *